United States Patent [19]
Caldwell et al.

[11] Patent Number: 5,204,015
[45] Date of Patent: Apr. 20, 1993

[54] SUBTILISIN MUTANTS

[75] Inventors: Robert M. Caldwell, San Carlos; David A. Estell, San Mateo; Thomas P. Graycar, Pacifica, all of Calif.

[73] Assignee: Genencor International, Inc., So. San Francisco, Calif.

[21] Appl. No.: 958,885

[22] Filed: Oct. 9, 1992

Related U.S. Application Data

[60] Division of Ser. No. 600,430, Oct. 19, 1990, which is a continuation-in-part of Ser. No. 429,882, Oct. 31, 1989, abandoned, Ser. No. 84,589, Aug. 12, 1987, abandoned, Ser. No. 294,340, Jan. 6, 1989, Pat. No. 5,155,033, Ser. No. 86,869, Aug. 21, 1987, abandoned, and Ser. No. 92,976, Sep. 3, 1987, abandoned, said Ser. No. 294,340, is a continuation-in-part of Ser. No. 35,652, Apr. 6, 1987, abandoned, which is a continuation-in-part of Ser. No. 858,594, Apr. 30, 1986, abandoned, which is a continuation of Ser. No. 614,612, May 29, 1984, Pat. No. 5,081,616, Ser. No. 614,615, May 29, 1984, abandoned, Ser. No. 614,617, May 29, 1984, abandoned, and Ser. No. 614,491, May 29, 1984, abandoned.

[51] Int. Cl.⁵ .............................................. C11D 10/00
[52] U.S. Cl. ......................... 252/174.12; 252/DIG. 12
[58] Field of Search ................................... 252/174.12

*Primary Examiner*—Robert A. Wax
*Assistant Examiner*—G. Bugaisky
*Attorney, Agent, or Firm*—Margaret A. Horn

[57] ABSTRACT

Novel carbonyl hydrolase mutants derived from the DNA sequences of naturally-occurring or recombinant non-human carbonyl hydrolases are disclosed. The mutant carbonyl hydrolases, in general, are obtained by in vitro modification of a precursor DNA sequence encoding the naturally-occurring or recombinant carbonyl hydrolase to generate the substitution of one or more amino acid residues in the amino acid sequence of a precursor carbonyl hydrolase. Such mutant carbonyl hydrolases have properties which are different from those of the precursor hydrolase and are especially useful in detergent formulations. The substituted amino acid residues correspond to position +123 and/or +274 in *Bacillus amyloliquefaciens* subtilisin.

4 Claims, 14 Drawing Sheets

FIG-1B

```
                                        -1  1                              10                                                    20
                          His  Bal  Ala  His  Ala  Tyr  Ala  Gln  Ser  Val  Pro  Tyr  Gly  Val  Ser  Gln  Ile  Lys  Ala  Pro  Ala  Leu  His  Ser  Gln
399                       CAC  GTA  GCA  CAT  GCG  TAC  GCG  CAG  TCC  GTG  CCT  TAC  GGC  GTA  TCA  CAA  ATT  AAA  GCC  CCT  GCT  CTG  CAC  TCT  CAA 20                                                           30                                                 40
      Gly  Tyr  Thr  Gly  Ser  Asn  Val  Lys  Val  Ala  Val  Ile  Asp  Ser  Gly  Ile  Asp  Ser  Ser  His  Pro  Asn  Leu  Lys  Val
474   GGC  TAC  ACT  GGA  TCA  AAT  GTT  AAA  GTA  GCG  GTT  ATC  GAC  AGC  GGT  ATC  GAT  TCT  TCT  CAT  CCT  AAT  TTA  AAG  GTA

Pro  Asn                                60  Asp
      Ala  Gly  Gly  Ala  Ser  Met  Val  Pro  Asn  Pro  Phe  Gln  Asp  Asn  Asn  Ser  Asp  Ser  His  Gly  Thr  His  Val  Ala
549   GCA  GGA  GGA  GCC  AGC  ATG  GTT  CCT  AAT  CCT  TTC  CAA  GAC  AAC  AAC  TCT  GAT  TCT  CAC  GGA  ACT  CAC  GTT  GCC

Asp  Ala  100                                                              Ser  Ala
      Gly  Thr  Val  Ala  Ala  Leu  Asn  Asn  Ser  Ile  Gly  Val  Leu  Gly  Val  Ala  Pro  Ser  Ala  Ser  Leu  Tyr  Ala  Val  Lys
624   GGC  ACA  GTT  GCG  GCT  CTT  AAT  AAT  TCA  ATC  GGT  GTA  TTA  GGC  GTT  GCG  CCA  AGC  GCA  TCA  CTT  TAC  GCT  GTA  AAA

Val  Leu  Gly  Ala  Asp  Gly  Ser  Gly  Gln  Tyr  Ser  Trp  Ile  Ile  Asn  Gly  Ile  Glu  Trp  Ala  Ile  Ala  Asn  Asn  Met
699   GTT  CTC  GGT  GCT  GAC  GGT  TCC  GGC  CAA  TAC  AGC  TGG  ATC  ATT  AAC  GGA  ATC  GAG  TGG  GCG  ATC  GCA  AAC  AAT  ATG 120                                          130                                                  140
      Asp  Val  Ile  Asn  Met  Ser  Leu  Gly  Gly  Pro  Ser  Gly  Ser  Ala  Ala  Leu  Lys  Ala  Ala  Val  Asp  Lys  Ala  Val  Ala
774   GAC  GTT  ATT  AAC  ATG  AGC  CTC  GGC  GGA  CCT  TCT  GGT  TCT  GCT  GCT  TTA  AAA  GCG  GCA  GTT  GAT  AAA  GCC  GTT  GCA

150                                      Ser  Thr  160
      Ser  Gly  Val  Val  Val  Val  Ala  Ala  Ala  Gly  Asn  Glu  Gly  Ser  Ser  Gly  Ser  Ser  Ser  Thr  Val  Gly  Tyr  Pro  Gly
849   TCC  GGC  GTC  GTA  GTC  GTT  GCG  GCA  GCA  GGC  AAC  GAA  GGA  TCC  AGC  GGC  AGC  TCA  AGC  ACA  GTG  GGC  TAC  CCT  GGT
```

```
       170
     Lys Tyr Pro Ser Val Ile Ala Val Gly Ala Val Asp Ser Ser Asn Gln Arp Ala Ser Phe Ser Ser Val Gly Pro
 924 AAA TAC CCT TCT GTC ATT GCA GTT GGC GCT GTT GAC AGC AGC AAC CAA AGA GCA TCT TTC TCA AGC GTA GGA CCT
                                              180                                    190
     Glu Leu Asp Val Met Ala Pro Gly Val Ser Ile Gln Ser Thr Leu Pro Gly Asn Lys Tyr Gly Ala Tyr Asn Gly
 999 GAG CTT GAT GTC ATG GCA CCT GGC GTA TCT ATC CAA AGC ACG CTT CCT GGA AAC AAA TAC GGG GCG TAC AAC GGT
                       200                                    210
     Thr Ser Met Ala Ser Pro His Val Ala Gly Aal Ala Ala Leu Ile Leu Ser Lys His Pro Asn Trp Thr Asn Thr
1074 ACG TCA ATG GCA TCT CCG CAC GTT GCC GGA GCG GCT GCT TTG ATT CTT TCT AAG CAC CCG AAC TGG ACA AAC ACT
              220                                    230                                    240
     Gln Val Aro Ser Ser Leu Glu Asn Thr Thr Thr Lys Leu Gly Asp Ser Phe Tyr Tyr Gly Lys Gly Leu Ile Asn
1149 CAA GTC CGC AGC AGT TTA GAA AAC ACC ACT ACA AAA CTT GGT GAT TCT TTG TAC TAT GGA AAA GGG CTG ATC AAC
                    250                                    260
     Val Gln Ala Ala Ala Gln DC
     270                275                              TERM
1224 GTA CAA GCG GCA GCT CAG TAA  AACATAAAAACCGGCCTTGGCCCCCGGTTTTTATTATTTTCTTCCTCCGCATGTTCAATCCGCTCC
1316 ATAATCGACGGATGGCTCCCTCTGAAAATTTAACGAGAAACGGGGTTGACCCGGCTCAGTCCGGTAACGGCCAACTCCTGAAACGTCTCAATCGCCG
1416 CTTCCCGGTTTCCGGTCAGCTCAATGCCATAACGGTCGGCGGCGTTTCCTGATACGGGAGACGGCATTCGTAATCGGATC
```

FIG.-1C

TOTALLY CONSERVED RESIDUES IN SUBTILISINS

Homology of Bacllur proteases

1. Bacillus amyloliquifaciens
2. Bacillus subtilis var.I168
3. Bacillus licheniformis (carlsbergensis)

PREFERRED MUNTANT ─────┐
BACILLUS LENTUS ──────┐│
BACILLUS AMYLOLIQUIFACIENS ─┐││
```
01        10        20        30
AQSVPYGVSQIKAPALHSQGYTGSNVKVAVIDSGIDSSHP ─┘││
AQSVPWGISRVQAPAAHNRGLTGSGVKVAVLDTGI*STHP ──┘│
AQSVPWGISRVQAPAAHNRGLTGSGVRVAVLDTGI*STHP ───┘

41        50        60        70
DLKVAGGASMVPSETNPFQDNNSHGTHVAGTVAALNNSIG
DLNIRGGASFVPGE*PSTQDGNGHGTHVAGTIAALNNSIG
DLNIRGGASFVPGE*PSTQDGNGHGTHVAGTIAALNNSIG 81        90        100       110
VLGVAPSASLYAVKVLGADGSGQYSWIINGIEWAIANNMD
VLGVAPSAELYAVKVLGASGSGSVSSIAQGLEWAGNNGMH
VLGVAPSAELYAVKVLGASGSGSYSSIAQGLEWAGNNGMH 121       130       140       150
VINMSLGGPSGSSAALKAAVDKAVSGVVVVAAAGNEGTSG
VANLSLGSPSPSATLEQAVNSATSRGVLVVAASGNSGAGS
VASLSLGSPSPSATLEQAVNSATSRGVLVVAASGNSGAGS 161       170       180       190
SSSTVGYPGKYPSVIAVGAVDSSNQRASFSSVGPELDVMA
****ISYPARYANAMAVGATDQNNNRASFSQYGAGLDIVA
****ISYPARYANAMAVGATDQNNNRASFSQYGAGLDIVA 201       210       220       230
PGVSIQSTLPGNKYGAYNGTSMASPHVAGAAALILSKHPN
PGVNVQSTYPGSTYASLNGTSMATPHVAGAAALVKQKNPS
PGVNVQSTYPGSTYASLNGTSMATPHVAGAAALVKQKNPS 241       250       260       270
WTNTQVRSSLENTITKLGDSFYYGKGLINVQAAAQ
WSNVQIRNHLKNTATSLGSTNLYGSGLVNAEAATR
WSNVQIRNHLKNTATSLGSTNLYGSGLVNAEAAAR
```

FIG.-4

Sequence of synthetic DNA linker (fragment #2)

5'-G-ATC-GTC-GCG-TCG-ACC-GCA-CTA-CTC-ATT-TCT-GTT-GCT-TTT-AGT-TCA-T-3'
3'-CAG-CGC-AGC-TGG-CGT-GAT-GAG-TAA-AGA-CAA-CGA-AAA-TCA-AGT-AGC-5'

```
                    110                     115                     120                     125
W.T. A.A.:          Gly Leu Glu Trp Ala Gly Asn Asn Gly Met His Val Ala Asn Leu Ser Leu Gly

W.T. DNA:           GGC TTA GAA TGG GCT GGC AAC AAC GGC ATG CAC GTT GCT AAC TTA AGC CTC GGG-3'
                    CCG AAT CTT ACC CGA CCG TTG TTG TAC GTG CAA CGA ATT TCG GAG CCC-5'
                                                            SphI                        AvaI

* **
pX123 DNA:          GGC CTC GAG TGG GCT GGC AAC AAC GGC ATG CAC GTT GCT AAC TTA AGC CTC GGG-3'
                    CCG GAG CTC ACC CGA CCG TTG TTG TAC GTG CAA CGA ATT TCG GAG CCC-5'
                        XhoI                            SphI                        AvaI pX123 cut           GGC C                                                               pTC GGG-3'
w/ XhoI             CCG GAG CTp                                                             C-5'
and AvaI:

*
Cut pX1213          GGC CTC GAG TGG GCT GGC AAC AAC GGT ATG CAC GTT GCT XXX TTA AGC CTC GGG-3'
ligated w/          CCG GAG CTC ACC CGA CCG TTG TTG CCA TAC GTG CAA CGA XXX AAT TCG GAG CCC-5'
duplex DNA              XhoI                            SphI destroyed   123
cassettes:
```

```
  1   GCG CAA TCA GTG CCA TGG GGC ATC TCG CGA GTT CAA GCT CCT GCT CAC AAC CGC GGC
  1   Ala Gln Ser Val Pro Trp Gly Ile Ser Arg Val Gln Ala Pro Ala His Asn Arg Gly

61   TTA ACA GGC AGC GTT GGC ATT AGA GGC TTC GTT GCT GAT TTA GCT ATC AGC ACA --- CAC CCA
 21   Leu Thr Gly Ser Val Gly Ile Arg Gly Phe Val Ala Asp Leu Ala Ile Ser Thr  -  His Pro

121   GAT CTT AAT ATT AGA GGC GGG GCG AGC TTC GTT CCC GGC GAA --- CCG ACA TCG ACA CAA GAT
 41   Asp Leu Asn Ile Arg Gly Gly Ala Ser Phe Val Pro Gly Glu  -  Pro Ser Thr Thr Gln Asp

181   GGC AAC GGC CAC ACA GGC CAC GTT GCC ACA ATC GCT TTA AAC AAC TCG ATC GGA
 61   Gly Asn Gly His Thr Gly His Val Ala Thr Ile Ala Leu Asn Asn Ser Ile Gly

241   GTT TTA GGC GTT GCT CCT TCG GCC GAA TTA TAC GCT GTT AAA GTT TTA GGC GCT AGC GGC
 81   Val Leu Gly Val Ala Pro Ser Ala Glu Leu Tyr Ala Val Lys Val Leu Gly Ala Ser Gly

301   AGC GGC TAC AGC TCT ATC ATC GCT CAA GGC CTC GAG TGG GCT AAC AAC GGT AGT CAC
101   Ser Gly Tyr Ser Ser Ile Ile Ala Gln Gly Leu Glu Trp Ala Asn Asn Gly Met His

361   GTT GCT AGC TTA AGC CTC TGG AGC CCT AGC GCT ACA TTA GAA CAA GCT GTT AAC
121   Val Ala Ser Leu Ser Leu Trp Ser Pro Ser Ala Thr Leu Glu Gln Ala Val Asn
```

FIG.-10B

```
421 AGC GCT ACA TCT AGA GGC GTT TTA GTT GCT GCG AGC GGC AAC AGC GGC GCT GGA TCG
141 Ser Ala Thr Ser Arg Gly Val Leu Val Ala Ala Ser Gly Asn Ser Gly Ala Gly Ser

481 --- --- --- --- --- --- --- AGC CTA ATA CGC TAA TGC CAT GGC TGT TGG CGC ACA
161  -   -   -   -   -   -   -  Ser tyr Ala Arg Asn Ala Met Ala Val Gly Ala Thr 541 GAT CAA AAC AAC AGA GCA TTC AGT CAA TAC GGC GCT GGC TTA GAT ATC GTG GCG
181 Asp Gln Asn Asn Arg Ala Ser Phe Ser Gln Tyr Gly Ala Gly Leu Asp Ile Val Ala 601 CCT GGC GTT AAC GTT CAA ACA TAC CCT AGC GCC TTG AAC GGT ACA
201 Pro Gly Val Asn Val Gln Ser Thr Tyr Pro Gly Ser Ala Ser Leu Asn Gly Thr 661 TCG ATG GCG ACA CCT CAC GTT GCC GGA GCG GCT GCA CTA GTT AAA CAA AAA CCT TCA
221 Ser Met Ala Thr Pro His Val Ala Gly Ala Ala Leu Val Lys Gln Lys Pro Ser 721 TGG AGC AAC GTT CAA ATC CGC AAC CAC TTA AAA ACA GCT ACT AGC TTA GGC AGT ACT
241 Trp Ser Asn Val Gln Ile Arg Asn His Leu Lys Asn Thr Ala Thr Ser Leu Gly Ser Thr 781 AAC TTA TAC GGC AGC GGC TTA GTT AAC GCT GAA GCT GCA GCT CGT
261 Asn Leu Tyr Gly Ser Gly Leu Val Asn Ala Glu Ala Ala Ala Arg
```

SUBTILISIN MUTANTS

This is a Division of application Ser. No. 600,430 filed Oct. 19, 1990, which is a continuation-in-part of U.S. patent application Ser. No. 429,882 filed Oct. 31, 1989 abandoned. It is also a continuation-in-part of U.S. patent application Ser. No. 084,589 filed Aug. 12, 1987 abandoned, of U.S. patent application Ser. No. 294,340 filed Jan. 6, 1989 now U.S. Pat. No. 5,155,033, of U.S. patent application Ser. No. 086,869 filed Aug. 21, 1987 abandoned, U.S. patent application Ser. No. 092,976 filed Sep. 3, 1987 abandoned, of U.S. patent application Ser. No. 294,340 filed Jun. 14, 1990 which is a continuation-in-part of U.S. patent application Ser. No. 035,652 filed Apr. 6, 1987 which is a continuation-in-part of U.S. patent application Ser. No. 858,594 filed Apr. 4, 1986 abandoned which is a continuation of U.S. patent application Ser. No. 614,612, 614,615, 614,617 and 614,491, all filed May 29, 1984. U.S. patent application Ser. No. 614,612 issued as U.S. Pat. No. 5,081,616 on Jul. 26, 1988 abandoned.

FIELD OF THE INVENTION

The present invention relates to novel carbonyl hydrolase mutants having an amino acid sequence wherein one or more amino acid residues of a precursor carbonyl hydrolase, specifically those at positions corresponding to residues +123 and/or +274 in *Bacillus amyloliquefaciens* subtilisin, have been substituted with a different amino acid. Such mutant carbonyl hydrolases, in general, are obtained by in vitro modification of a precursor DNA sequence encoding a naturally-occurring or recombinant carbonyl hydrolase to encode the substitution of one or both of these amino acid residues in a precursor amino acid sequence alone or in combination with other substitution, insertion or deletion in the precursor amino acid sequence.

BACKGROUND OF THE INVENTION

Serine proteases are a subgroup of carbonyl hydrolase. They comprise a diverse class of enzymes having a wide range of specificities and biological functions. Stroud, R. M. (1974), *Sci. Amer.*, 131, 74–88. Despite their functional diversity, the catalytic machinery of serine proteases has been approached by at least two genetically distinct families of enzymes: the subtilisins and the mammalian chymotrypsin related and homologous bacterial serine proteases (e.g., trypsin and *S. gresius* trypsin). These two families of serine proteases show remarkably similar mechanisms of catalysis. Kraut, J. (1977), *Ann. Rev. Biochem.*, 46, 331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW 27,500) which is secreted in large amounts from a wide variety of Bacillus species and other microorganisms. The protein sequence of subtilisin has been determined from at least four different species of Bacillus. Markland, F. S., et al. (1983), *Honne-Seyler's Z. Physiol. Chem.*, 364, 1537–1540. The three-dimensional crystallographic structure of *Bacillus amyloliquefaciens* subtilisin to 2.5A resolution has also been reported. Wright, C. S., et al. (1969), *Nature*, 221, 235–242; Drenth, J., et al. (1972), *Eur. J. Biochem.*, 26, 177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972), *Biochemistry*, 11, 2439–2449), or product complexes (Robertus, J. D., et al. (1976), *J. Biol. Chem.*, 251, 1097–1103), have also provided information regarding the active site and putative substrate binding cleft of subtilisin. In addition, a large number of kinetic and chemical modification studies have been reported for subtilisin (Philipp, M., et al. (1983), *Mol. Cell. Biochem.*, 51, 5–32; Svendsen, B. (1976), *Carlsberg Res. Comm.*, 41, 237–291; Markland, F. S. Id.) as well as at least one report wherein the side chain of methione at residue 222 of subtilisin was converted by hydrogen peroxide to methionine-sulfoxide (Stauffer, D. C., et al. (1965), *J. Biol. Chem.*, 244, 5333–5338) and the side chain of serine at residue 221 converted to cysteine by chemical modification (Polgar, et al. (1981), *Biochimica et Biophysica Acta*, 667, 351–354.)

U.S. Pat. No. 4,760,025 and EPO Publication No. 0 130 756 published Jan. 9, 1985 each disclose the modification of subtilisin amino acid residues corresponding to positions in *Bacillus amyloliquefacien* subtilisin tyrosine −1, aspartate +32, asparagine +155, tyrosine +104, methionine +222, glycine +166, histidine +64, glycine +169, phenylalanine +189, serine +33, serine +221, tyrosine +217, glutamate +156 and alanine +152. EPO Publication No. 0 251 446 published Jan. 7, 1988 discloses other amino acid residues in *Bacillus amyloliquefaciens* subtilisin and their equivalents which may be modified by way of substitution, insertion or deletion and which may be combined with modifications to the residues identified in U.S. Pat. No. 4,760,025 to form useful subtilisin mutants. The particular residues identified herein, however, are not identified in these references.

Similarly, PCT Publication No. WO 89/09819 and WO 89/09830 each published Oct. 19, 1989, disclose subtilisin enzymes made by mutating a nucleotide sequence coding for a subtilisin. Numerous amino acid residues are identified in each of these publications which may be so modified. However, as with the previously identified references, neither identifies the residues of the present invention.

Accordingly, it is an object herein to provide carbonyl hydrolase mutants containing the substitution of amino acid residues in a precursor carbonyl hydrolase corresponding to positions +123 and/or +274 in *Bacillus amyloliquefaciens* subtilisin. Such mutants generally have at least one property which is different from the same property of the carbonyl hydrolase precursor from which the amino acid of said mutant is derived.

It is further object to provide DNA sequences encoding such carbonyl hydrolase mutants as well as expression vectors containing such mutant DNA sequences.

Still further, another object of the invention is to provide host cells transformed with such vectors as well as host cells which are capable of expressing such DNA to produce carbonyl hydrolase mutants either intracellularly or extracellularly.

The references discussed above are provided solely for their disclosure prior to the filing date of the instant case, and nothing herein is to be construed as an admission that the inventors are not entitled to antidate such disclosure by virtue of a prior invention or priority based on earlier filed applications.

SUMMARY OF THE INVENTION

The invention includes non-naturally occurring carbonyl hydrolase mutants having a different proteolytic activity, stability, and/or performance characteristic as compared to the precursor carbonyl hydrolase from which the amino acid sequence of the mutant is derived. The precursor carbonyl hydrolase may be a naturally-occurring carbonyl hydrolase or recombinant hydrolase. Specifically, such carbonyl hydrolase mutants have an amino acid sequence, not found in nature, which is derived by replacement of one or more amino acid residues of a precursor carbonyl hydrolase with one or more different amino acids. The one or more amino acid residues of the precursor enzyme correspond to positions Asn +123 and/or Ala +274 of *Bacillus amyloliquefaciens* subtilisin or equivalent amino acid residues in other carbonyl hydrolases or subtilisins.

The invention also includes mutant DNA sequences encoding such carbonyl hydrolase or subtilisin mutants. These mutant DNA sequences are derived from a precursor DNA sequence which encodes a naturally-occurring or recombinant precursor enzyme. The mutant DNA sequences are derived by modifying the precursor DNA sequence to encode the substitution of one or more specific amino acid residues encoded by the precursor DNA sequence corresponding to position +123 and/or +274 in *Bacillus amyloliquefaciens*. These recombinant DNA sequences encode carbonyl hydrolase mutants having a novel amino acid sequence and, in general, at least one property which is substantially different from the same property of the enzyme encoded by the precursor carbonyl hydrolase DNA sequence. Such properties include proteolytic activity, stability and/or enhanced performanc characteristics.

The invention also includes procaryotic and eucaryotic subtilisins with a different amino acid residue such as serine, at positions equivalent to Asn +123 in *Bacillus amyloliquefaciens* subtilisin and to subtilisin with different amino acid residues at positions equivalent to position +274 in *Bacillus amyloliquefaciens* subtilisin.

Further, the invention includes expression vectors containing such mutant carbonyl hydrolase DNA sequences as well as host cells transformed with such vectors which are capable of producing such mutants. The invention also relates to detergent compositions comprising the carbonyl hydrolase mutants of the invention.

BRIEF DESCRIPTION OF THE DRAWINGS

FIG. 2 depicts the conserved amino acid residues among subtilisins from *Bacillus amyloliquefaciens*, *Bacillus subtilis* var I168 and *Bacillus licheniformis* (carlsbergensis).

FIGS. 3A and 3B depict the amino acid sequence of subtilisin from *Bacillus amyloliquefaciens*, *Bacillus subtilis* var I168 and *Bacillus licheniformis*.

FIG. 4 depicts the amino acid sequence of three subtilisins. The top line represents the amino acid sequence of subtilisin from *Bacillus amyloliquefaciens* subtilisin (also sometimes referred to as subtilisin BPN'). The second line depicts the amino acid sequence of subtilisin from *Bacillus lentus* (subtilisin 309 in PCT Publication No. WO89/06276). The bottom line represents the amino acid sequence of a preferred embodiment of the invention designated GG-RYSA. The symbol * denotes the absence of specific amino acid residues as compared to subtilisin BPN'.

FIG. 9 depicts the cassette used to make substitutions in the DNA at codon position +123 by cassette mutagenesis. XXX represents the codon modified to encode the amino acid substitutions at position +123.

FIG. 10(a-b) depict the DNA and amino acid sequence of a preferred embodiment of the invention wherein the DNA sequence is a synthetic DNA. The DNA in this Figure has been modified to encode arginine at position 27, serine at position 78, tyrosine at position 104, serine at position 123 and alanine at position 274.

DETAILED DESCRIPTION OF THE INVENTION

Figure 1A:
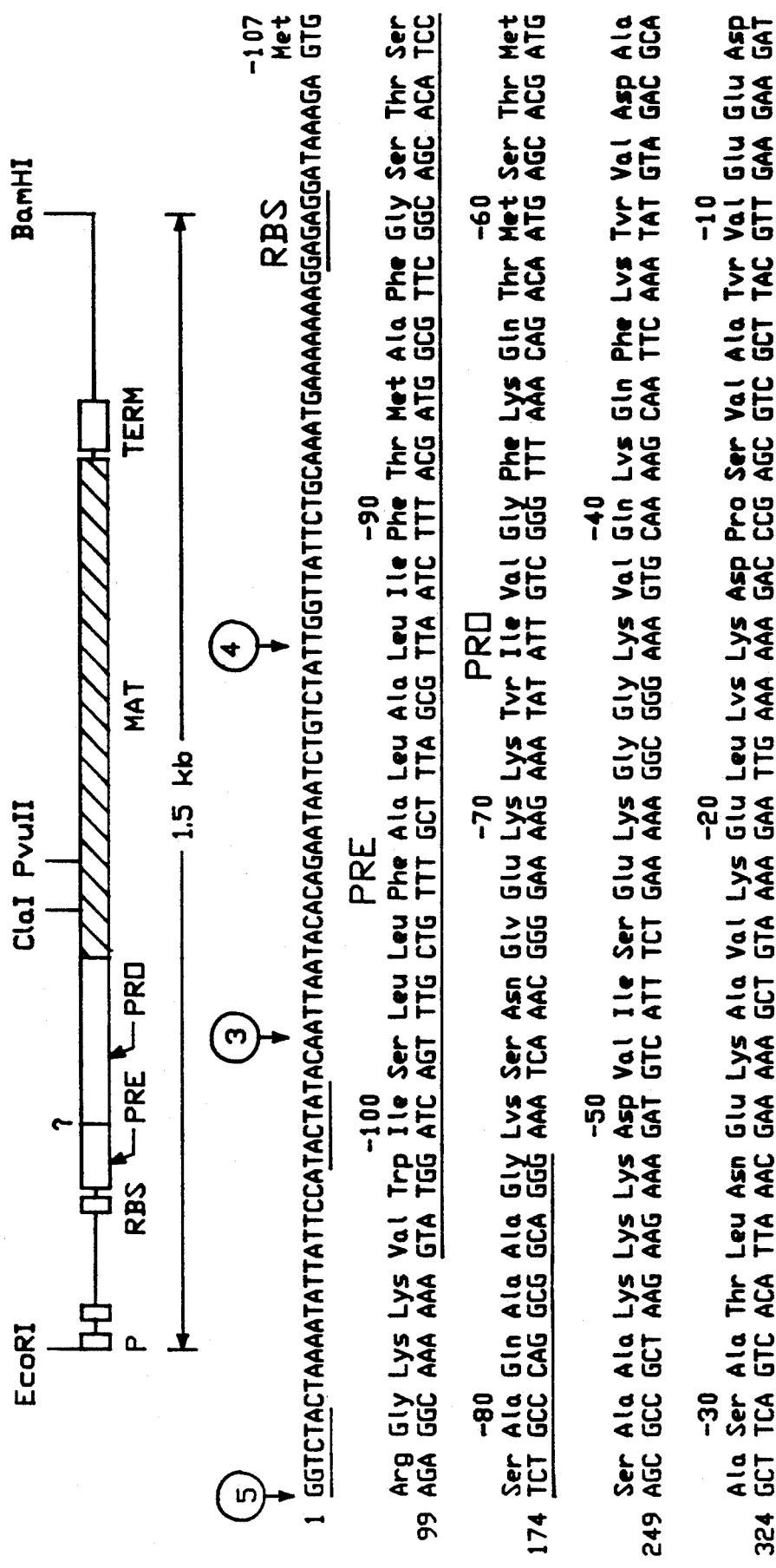
FIGS. 1(a-e) depict the DNA and amino acid sequence for *Bacillus amyloliquefacients* subtilisin and a partial restriction map of this gene.

It has been discovered that in vitro mutations in the carbonyl hydrolase subtilisin at an amino acid residue equivalent to +123 in *Bacillus amyloliquefaciens* subtilisin produces subtilisin mutants exhibiting altered proteolytic activity over precursor subtilisins.

It has also been discovered that in vitro mutation at residues equivalent to +274 in *Bacillus amyloliquefaciens* subtilisin produce subtilisin mutants exhibiting altered stability, e.g. modified autoproteolytic stability. In some instances, these latter mutants also exhibit enhanced performance when used in detergent compositions.

Carbonyl hydrolases are enzymes which hydrolyze compounds containing

bonds in which X is oxygen or nitrogen. They include naturally-occurring carbonyl hydrolases and recombinant carbonyl hydrolases. Naturally-occurring carbonyl hydrolases principally include hydrolases, e.g. peptide hydrolases, such as subtilisins or metalloproteases. Peptide hydrolases include α-aminoacylpeptide hydrolase, peptidylamino acid hydrolase, acylamino hydrolase, serinecarboxypeptidase, metallocarboxypeptidase, thiol proteinase, carboxylproteinase and metalloproteinase. Serine, metallo, thiol and acid proteases are included, as well as endo and exo-proteases.

"Recombinant carbonyl hydrolase" refers to a carbonyl hydrolase in which the DNA sequence encoding the naturally-occurring carbonyl hydrolase is modified to produce a mutant DNA sequence which encodes the substitution, insertion or deletion of one or more amino acids in the carbonyl hydrolase amino acid sequence. Suitable modification methods are disclosed herein, in EPO Publication No. 0 130 756 published Jan. 9, 1985 and EPO Publication No. 0 251 446 published Jan. 7, 1988.

Subtilisins are bacterial or fungal carbonyl hydrolases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus is aspartate-histidine-serine. In the chymotrypsin related proteases the relative order, however is histidine-aspartate-serine. Thus, subtilisin herein refers to a serine protease having the catalytic triad of subtilisin related proteases. Examples include the subtilisins identified in FIG. 3 herein and as described in PCT Publication WO89/06276 and EPO Publication No. 0 283 075.

"Recombinant subtilisin" refers to a subtilisin in which the DNA sequence encoding the subtilisin is modified to produce a mutant DNA sequence which encodes the substitution, deletion or insertion of one or more amino acids in the naturally-occurring subtilisin amino acid sequence. Suitable methods to produce such modification and which may be combined with those disclosed herein include those disclosed in EPO Publication Nos. 0 130 756 and 0 251 446 and PCT Publication Nos. WO89/06279, WO89/09830 and WO89/09819.

"Non-human carbonyl hydrolases" and the DNA encoding them may be obtained from many procaryotic and eucaryotic organisms. Suitable examples of procaryotic organisms include gram negative organisms such as *E. coli* or Pseudomonas and gram positive bacteria such as Micrococcus or Bacillus. Examples of eucaryotic organisms from which carbonyl hydrolase and their genes may be obtained include yeast such as *Saccaromycees cerevisiae*, fungi such as Aspergillus sp., and non-human mammalian sources such as, for example, bovine sp. from which the gene encoding the carbonyl hydrolase chymosin can be obtained. As with subtilisins, a series of carbonyl hydrolases can be obtained from various related species which have amino acid sequences which are not entirely homologous between the members of that series but which nevertheless exhibit the same or similar type of biological activity. Thus, non-human carbonyl hydrolase as used herein has a functional definition which refers to carbonyl hydrolases which are associated, directly or indirectly, with procaryotic and eucaryotic sources.

A "carbonyl hydrolase mutant" has an amino acid sequence which is derived from the amino acid sequence of a "precursor carbonyl hydrolase". The precursor carbonyl hydrolases include naturally-occurring carbonyl hydrolases and recombinant carbonyl hydrolases. The amino acid sequence of the carbonyl hydrolase mutant is "derived" from the precursor hydrolase amino acid sequence by the substitution, deletion or insertion of one or more amino acids of the precursor amino acid sequence. Such modification is of the "precursor DNA sequence" which encodes the amino acid sequence of the precursor carbonyl hydrolase rather than manipulation of the precursor carbonyl hydrolase enzyme per se. Suitable methods for such manipulation of the precursor DNA sequence include methods disclosed herein and in EPO Publication Nos. 0 130 756 and 0 251 446.

Specific residues corresponding to positions +123 and +274 of *Bacillus amyloliquefaciens* subtilisin are identified herein for substitution. These amino acid position numbers refer to those assigned to the mature *Bacillus amyloliquefaciens* subtilisin sequence presented in FIG. 1. The invention, however, is not limited to the mutation of this particular subtilisin but extends to precursor carbonyl hydrolases containing amino acid residues at positions which are "equivalent" to the particular identified residues in *Bacillus amyloliquefaciens* subtilisin.

A residue (amino acid) of a precursor carbonyl hydrolase is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor carbonyl hydrolase is directly compared to the *Bacillus amyloliquefaciens* subtilisin primary sequence and particularly to a set of residues known to be invariant in all subtilisins for which sequence is known (FIG. 2). After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

Figure 3A:
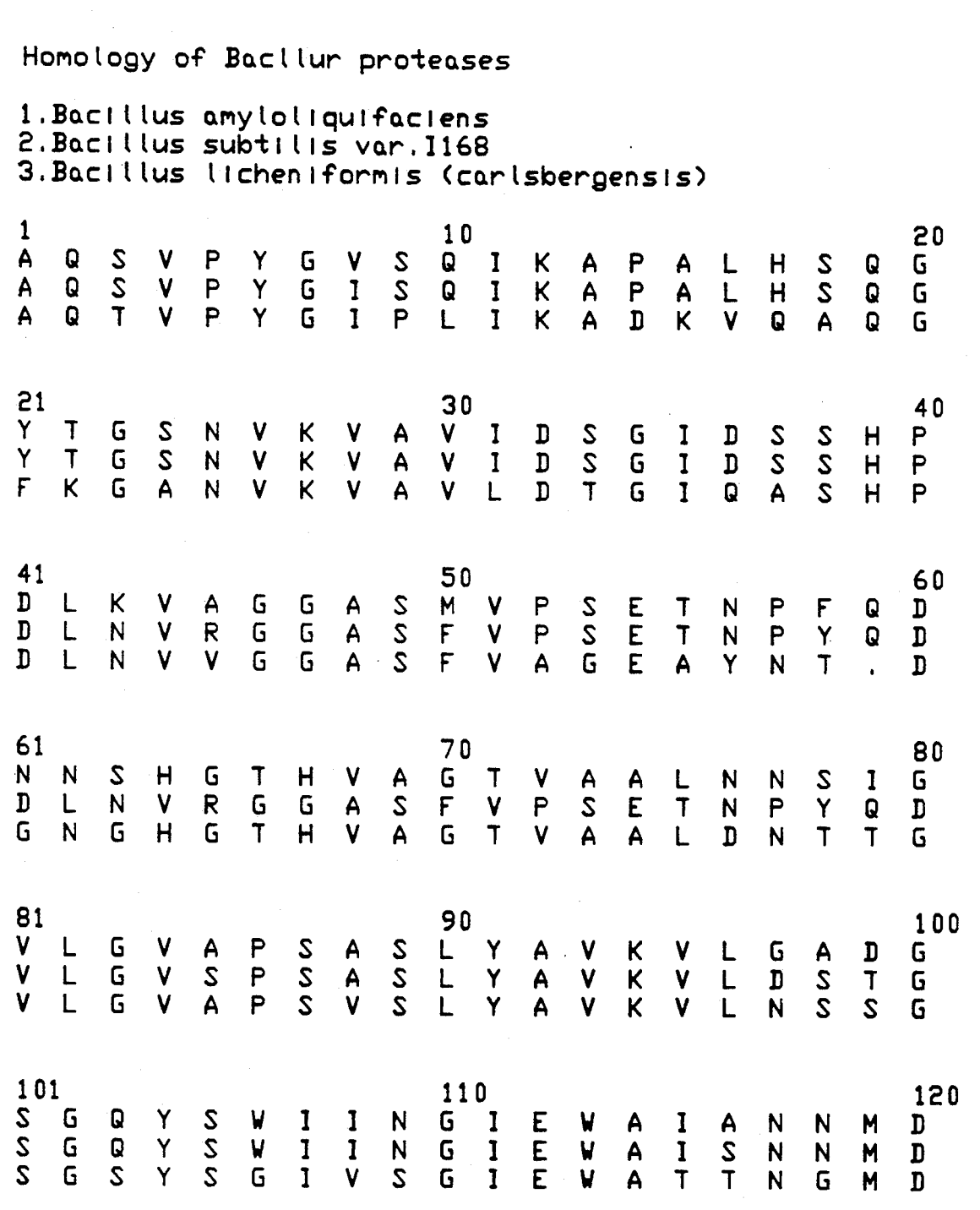
Figure 3B:
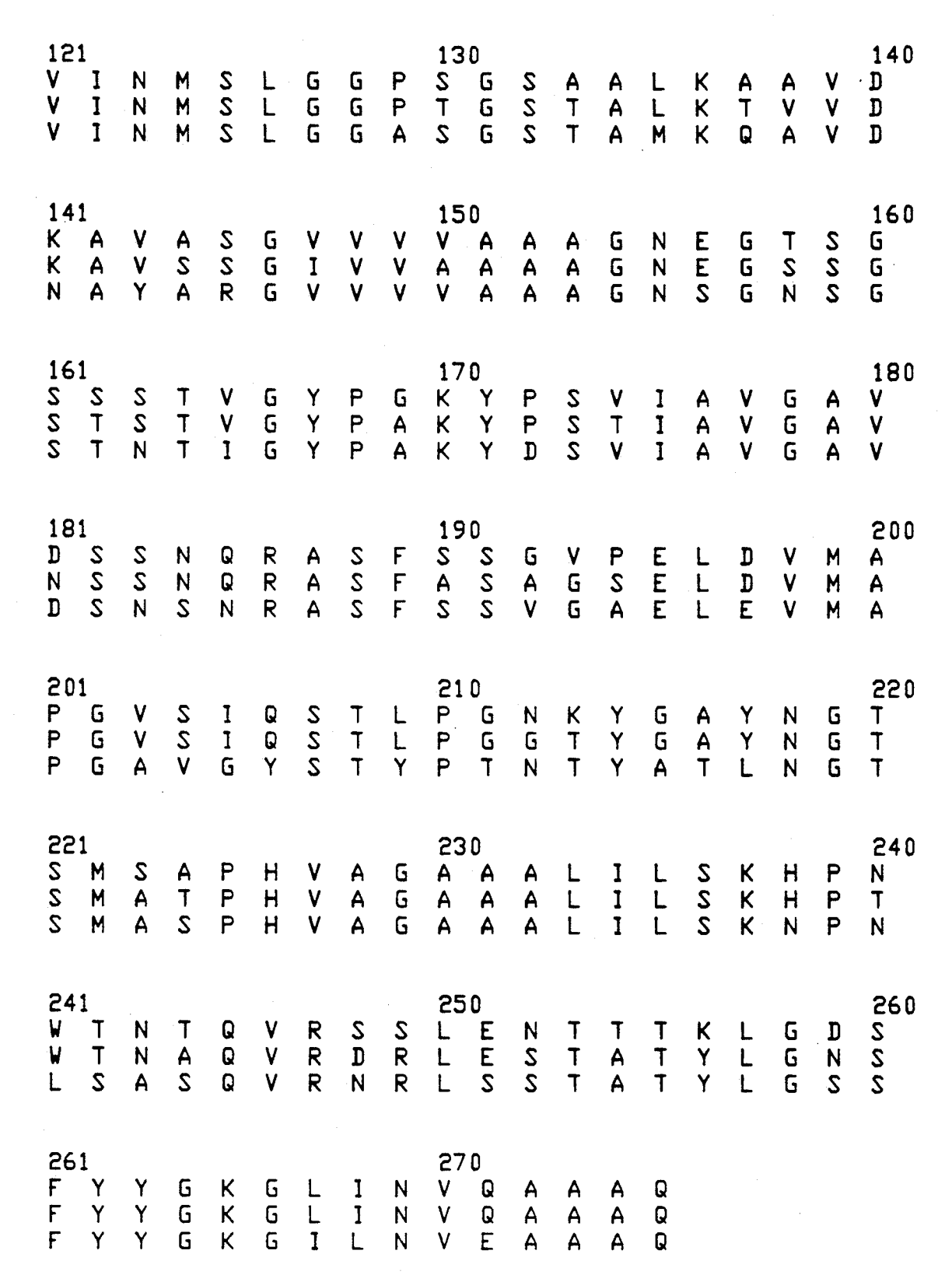

For example, in FIG. 3 the amino acid sequence of subtilisin from *Bacillus amyloliquefaciens*, *Bacillus subtilis* var. I168 and *Bacillus lichenformis* (carlsbergensis) are aligned to provide the maximum amount of homology between amino acid sequences. A comparison of these sequences shows that there are a number of conserved residues contained in each sequence. These are the residues identified in FIG. 2.

These conserved residues thus may be used to define the corresponding equivalent amino acid residues of *Bacillus amyloliquefaciens* subtilisin in other carbonyl hydrolases such as subtilisin from *Bacillus lentus* (PCT Publication No. WO89/06279 published Jul. 13, 1989) and the preferred subtilisin mutant herein. These particular amino acid sequences are aligned in FIG. 4 with the sequence of *Bacillus amyloliquefaciens* subtilisin to produce the maximum homology of conserved residues. As can be seen there are a number of deletions in the sequence of *Bacillus lentus* and in the preferred subtilisin mutant of the invention as compared to *Bacillus amyloliquefaciens* subtilisin. Thus, the equivalent amino acid for Val-165 in *Bacillus amyloliquefaciens* subtilisin in the other subtilisins is the particular isoleucine shown beneath Val-165.

In FIG. 4, the amino acid at position 123 is asparagine in *Bacillus amyloliquefaciens* subtilisin. In *Bacillus lentus* subtilisin the equivalent residue is the particular asparagine shown. In the preferred subtilisin mutant of the invention, however, the amino acid equivalent to +123 in *Bacillus amyloliquefaciens* subtilisin is an amino acid other than asparagine and is preferably the serine shown in FIG. 4. Similarly, in FIG. 4, the amino acid at position +274 *Bacillus amyloliquefaciens* subtilisin is alanine. As can be seen, the equivalent amino acid in *Bacillus lentus* subtilisin is the particular threonine shown in FIG. 4. In a particular preferred subtilisin mutant of the invention, the equivalent amino acid position 274 is occupied by the alanine shown in FIG. 4.

Thus, the positions +123 and +274 are identified by primary amino acid sequences in FIG. 4 for the subtilisin from *Bacillus lentus* and the preferred embodiment of the invention. However, various other amino acid residues may be modified which are equivalent to specific amino acids in *Bacillus amyloliquefaciens* subtilisin. Thus, in the preferred embodiment, the amino acid lysine at position 27 in *Bacillus amyloliquefaciens* subtilisin has an equivalent lysine at position 27 in *Bacillus lentus* subtilisin. As indicated in the Examples, the subtilisin comprising one of the preferred embodiments of the invention was derived by modifying a DNA sequence encoding *Bacillus lentus* subtilisin. Such modifications to the DNA included the modification of codons equivalent to positions 123 and 274 of *Bacillus amyloliquefaciens* subtilisin. However, two other modifications were made to the *Bacillus lentus* amino acid sequence at positions equivalent to residues 27 and 104 in *Bacillus amyloliquefaciens* subtilisin. Thus, as can be seen in FIG. 4, the lysine at equivalent residue 27 in *Bacillus lentus* subtilisin was modified to encode arginine in the preferred embodiment. Similarly, the valine residue at position 104 of *Bacillus lentus*, which is equivalent to tyrosine 104 in *Bacillus amyloliquefaciens* subtilisin, was also modified to encode tyrosine. Thus, the preferred embodiment shown in FIG. 4 contains an amino acid sequence derived from *Bacillus lentus* subtilisin by modifying residues of that subtilisin equivalent to positions 27, 104, 123 and 274 of *Bacillus amyloliquefaciens* subtilisin.

Equivalent residues may also be defined by determining homology at the level of tertiary structure for a precursor carbonyl hydrolase whose tertiary structure has been determined by x-ray crystallography. Equivalent residues are defined as those for which the atomic coordinates of two or more of the main chain atoms of a particular amino acid residue of the precursor carbonyl hydrolase and *Bacillus amyloliquefaciens* subtilisin (N on N, CA on CA, C on C, and O on O) are within 0.13 nm and preferably 0.1 nm after alignment. Alignment is achieved after the best model has been oriented and positioned to give the maximum overlap of atomic coordinates of non-hydrogen protein atoms of the carbonyl hydrolase in question to the *Bacillus amyloliquefaciens* subtilisin. The best model is the crystallographic model giving the lowest R factor for experimental diffraction data at the highest resolution available.

$$R \text{ factor} = \frac{\Sigma_h |F_o(h)| - |F_c(h)|}{\Sigma_h |F_o(h)|}$$

Equivalent residues which are functionally analogous to a specific residue of *Bacillus amyloliquefaciens* subtilisin are defined as those amino acids of the precursor carbonyl hydrolases which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor carbonyl hydrolase (for which a tertiary structure has been obtained by x-ray crystallography), which occupy an analogous position to the extent that although the main chain atoms of the given residue may not satisfy the criteria of equivalence on the basis of occupying a homologous position, the atomic coordinates of at least two of the side chain atoms of the residue lie with 0.13 nm of the corresponding side chain atoms of *Bacillus amyloliquefaciens* subtilisin. The coordinates of the three dimensional structure of *Bacillus amyloliquefaciens* subtilisin are set forth in EPO Publication No. 0 251 446 and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a mutant which has an amino acid sequence that does not correspond to one found in nature. In the case of conserved residues, such replacements should not result in a naturally-occurring sequence. The carbonyl hydrolase mutants of the present invention include the mature forms of carbonyl hydrolase mutants as well as the pro- and prepro-forms of such hydrolase mutants. The prepro-forms are the preferred construction since this facilitates the expression, secretion and maturation of the carbonyl hydrolase mutants.

"Prosequence" refers to a sequence of amino acids bound to the N-terminal portion of the mature form of a carbonyl hydrolase which when removed results in the appearance of the "mature" form of the carbonyl hydrolase. Many proteolytic enzymes are found in nature as translational proenzyme products and, in the absence of post-translational processing, are expressed in this fashion. A preferred prosequence for producing carbonyl hydrolase mutants, specifically subtilisin mutants, is the putative prosequence of *Bacillus amyloliquefaciens* subtilisin although other subtilisin prosequences may be used. In the Examples, the putative pro sequence from the subtilisin from *Bacillus lentus* (ATCC 21536) was used.

A "signal sequence" or "presequence" refers to any sequence of amino acids bound to the N-terminal portion of a carbonyl hydrolase or to the N-terminal portion of a prohydrolase which may participate in the secretion of the mature or pro forms of the hydrolase. This definition of signal sequence is a functional one, meant to include all those amino acid sequences, encoded by the N-terminal portion of the subtilisin gene or other secretable carbonyl hydrolases, which participate in the effectuation of the secretion of subtilisin or other carbonyl hydrolases under native conditions. The present invention utilizes such sequences to effect the secretion of the carbonyl hydrolase mutants as defined herein. A preferred signal sequence used in the Examples comprises the first seven amino acid residues of the signal sequence from *Bacillus subtilis* subtilisin fused to the remainder of the signal sequence of the subtilisin from *Bacillus lentus* (ATCC 21536).

A "prepro" form of a carbonyl hydrolase mutant consists of the mature form of the hydrolase having a prosequence operably linked to the amino-terminus of the hydrolase and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in EPO Publication No. 0 130 756 to render them incapable of secreting enzymatically active endoprotease. A preferred host cell for expressing subtilisin is the Bacillus strain BG2036 which is deficient in enzymatically active neutral protease and alkaline protease (subtilisin). The construction of strain BG2036 is described in detail in EPO Publication No. 0 130 756 and further described by Yang, M. Y., et al. (1984), *J. Bacteriol.*, 160, 15–21. Other host cells for expressing subtilisin include *Bacillus subtilis* I168 (EPO Publication No. 0 130 756).

Host cells are transformed or transfected with vectors constructed using recombinant DNA techniques. Such transformed host cells are capable of either replicating vectors encoding the carbonyl hydrolase mutants or expressing the desired carbonyl hydrolase mutant. In the case of vectors which encode the pre or prepro form of the carbonyl hydrolase mutant, such mutants, when expressed, are typically secreted from the host cell into the host cell medium.

"Operably linked" when describing the relationship between two DNA regions simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor carbonyl hydrolase may be obtained in accord with the general methods described in EPO Publication Nos. 0 130 756 and 0 251 446. As can be seen from the examples disclosed therein, the methods generally comprise synthesizing labelled probes having putative sequences encoding regions of the hydrolase of interest, preparing genomic libraries from organisms expressing the hydrolase, and screening the libraries for the gene of interest by hybridization to the probes. Positively hybridizing clones are then mapped and sequenced.

The cloned carbonyl hydrolase is then used to transform a host cell in order to express the hydrolase. The hydrolase gen is then ligated into a high copy number plasmid. This plasmid replicates in hosts in the sense that it contains the well-known elements necessary for plasmid replication: a promoter operably linked to the gene in question (which may be supplied as the gene's own homologous promotor if it is recognized, i.e., transcribed, by the host), a transcription termination and polyadenylation region (necessary for stability of the mRNA transcribed by the host from the hydrolase gene in certain eucaryotic host cells) which is exogenous or is supplied by the endogenous terminator region of the hydrolase gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the hydrolase gene into host genome. This is facilitated by procaryotic and eucaryotic organisms which are particularly susceptible to homologous recombination.

Alternatively, a synthetic gene encoding a naturally-occurring or mutant precursor carbonyl hydrolase may be produced. In such an approach, the DNA and/or amino acid sequence of the precursor hydrolase is determined. Multiple, overlapping synthetic single-stranded DNA fragments are thereafter synthesized which upon hybridization and ligation produce a synthetic DNA encoding the precursor hydrolase. This approach provides several advantages over cloning the natural gene in that restriction sites may be interposed throughout the DNA without change in the amino acid sequence encoded so as to facilitate subsequent modification to form mutant carbonyl hydrolases. Further, the synthetic approach allows for adjusting the codon usage in the synthetic gene to conform with the codon bias for the particular expression hosts to be used. An example of synthetic gene construction is set forth in the Examples.

Once the naturally-occurring or synthetic precursor carbonyl hydrolase gene has been cloned, a number of modifications are undertaken to enhance the use of the gene beyond synthesis of the naturally-occurring precursor carbonyl hydrolase. Such modifications include the production of recombinant carbonyl hydrolases as disclosed in EPO Publication Nos. 0 130 756 and 0 251 446 and the production of carbonyl hydrolase mutants described herein.

The following cassette mutagenesis method may be used to facilitate the construction and identification of the carbonyl hydrolase mutants of the present invention although other methods including site-directed mutagenesis may be used. First, the naturally-occurring gene encoding the hydrolase is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the hydrolase gene so as to facilitate the replacement of the gene segment. However, any convenient restriction site which is not overly redundant in the hydrolase gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is enormously simplified by this method because all of the oligonucleotides can be synthesized so as to have the same restriction sites, and no synthetic linkers are necessary to create the restriction sites.

As used herein, proteolytic activity is defined as the rate of hydrolysis of peptide bonds per milligram of active enzyme. Many well known procedures exist for measuring proteolytic activity (K. M. Kalisz, "Microbial Proteinases", *Advances in Biochemical Engineering/Biotechnology*, A. Fiechter ed., 1988).

In one aspect of the invention, the objective is to secure a mutant carbonyl hydrolase having a greater (numerically large) proteolytic activity as compared to the precursor carbonyl hydrolase, thereby enabling the use of the enzyme to more efficiently act on a target substrate. Specific amino acids useful to obtain such results in subtilisin-type carbonyl hydrolases at residues equivalent to +123 in *Bacillus amyloliquefaciens* subtilisin are presented in the Examples. In some instances, lower proteolytic activity may be desirable. In such cases a decrease in proteolytic activity can be produced by substituting the amino acids identified in the examples at residues equivalent to +123 in *Bacillus amyloliquefaciens* subtilisin.

For precursor subtilisins wherein serine is not the residue at the position equivalent to +123 in *Bacillus amyloliquefaciens* the greatest proteolytic activity is obtained when serine is substituted in the precursor at position +123. Further, no naturally-occurring *Bacillus subtilisin* is known to exist which contains serine at a position equivalent to +123 in *Bacillus amyloliquefaciens* subtilisin. Based on the discovery that serine at this position enhances proteolytic activity, one skilled in the art can screen naturally-occurring *Bacillus subtilisin* to identify and clone a natural mutant containing serine at this position. Such natural *Bacillus subtilisin* mutants are within the scope of the invention.

Where the carbonyl hydrolase is from other than Bacillus and a serine is present at +123 in the precursor enzyme the substitution can be one that decreases proteolytic activity. This would be useful, for example, where the synthetic activity of the carbonyl hydrolases is desired (as for synthesizing peptides). One may wish to decrease this proteolytic activity which is capable of destroying the product of such synthesis.

In another aspect of the invention, it has been determined that residues equivalent to +274 in *Bacillus amyloliquefaciens* subtilisin are important in modulating the overall performance characteristics of the enzyme in detergent compositions. Thus, as set forth in the Examples, the threonine in *Bacillus lentus* subtilisin at equivalent position +274 can be mutated to alanine in the preferred embodiment to produce enhanced performance of the mutant enzyme. As also disclosed in the Examples, substitution of this residue with an amino acid other than threonine, e.g. leucine, serine, valine and alanine results in a decrease in the stability of the mutant. Such decrease in stability is believed to be the result of autocatalytic degradation of the mutant. Thus, modifications of residues equivalent to +274 in *Bacillus subtilisin* are capable of enhancing the overall performance of the enzyme in a detergent composition and modulating the overall stability of the enzyme. In this aspect of the invention, the objective is to secure a mutant carbonyl hydrolase having enhanced performance when used in a detergent composition as compared to the precursor carbonyl hydrolase. As used herein, enhanced performance in a detergent is defined as increased cleaning of certain enzyme sensitive stains such as grass or blood. This cleaning is determined by visual evaluation after a standard wash cycle.

A preferred embodiment of the invention is set forth in the Examples wherein the lysine at position 27 is substituted with arginine, the valine at position 104 is substituted with tyrosine, the asparagine at position 123 substituted with serine and the threonine at residue 274 is substituted with alanine in *Bacillus lentus* subtilisin. Although the stability of this enzyme is somewhat reduced as compared to the precursor *Bacillus lentus* subtilisin, the performance level of this enzyme in a detergent composition is substantially enhanced such that the same performance of this *Bacillus lentus* subtilisin mutant is obtained as compared to the unmodified *Bacillus lentus* subtilisin when using approximately one-half the amount of enzyme.

Based on the results obtained with this and other mutant subtilisins, it is apparent that residues in carbonyl hydrolases equivalent to positions +123 and +274 in *Bacillus amyloliquefaciens* are important to the proteolytic activity, performance and/or stability of these enzymes.

Many of the carbonyl hydrolase mutants of the invention, especially subtilisin, are useful in formulating various detergent compositions. A number of known compounds are suitable surfactants useful in compositions comprising the carbonyl hydrolase mutants of the invention. These include nonionic, anionic, cationic, anionic, or zwitterionic detergents, as disclosed in U.S. Pat. No. 4,404,128 to Barry J. Anderson and U.S. Pat. No. 4,261,868 to Jiri Flora, et al. The art is familiar with the different formulations which can be used as cleaning compositions.

Subtilisins of the invention can be formulated into known powdered and liquid detergents having pH between 6.5 and 12.0 at levels of about 0.01 to about 5% preferably 0.1% to .005%) by weight. These detergent cleaning compositions can also include other enzymes such as known proteases and amylases, as well as builders and stabilizers.

The addition of subtilisins of the invention to conventional cleaning compositions does not create any special use limitation. In other words, any temperature and pH suitable for the detergent is also suitable for the present compositions as long as the pH is within the above range, and the temperature is below the subtilisins of the invention denaturing temperature. In addition, subtilisins of the invention can be used in a cleaning composition without detergents, again either alone or in combination with builders and stabilizers.

The following is presented by way of example and is not to be construed as a limitation to the scope of the claims.

EXAMPLE 1

Constructions for Expression of *Bacillus lentus* Subtilisin Gene in *Bacillus subtilis*

Figure 5:
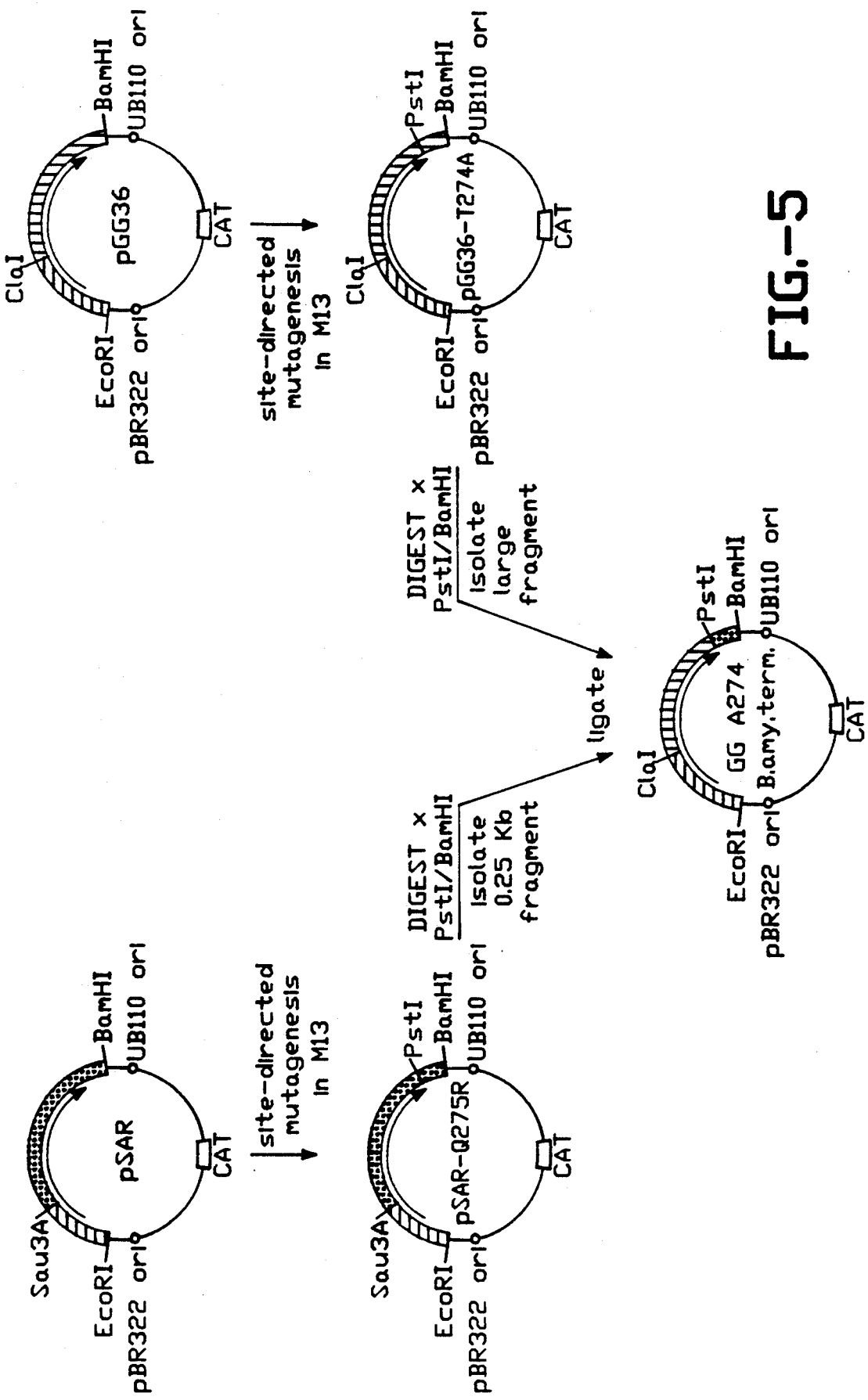
FIG. 5 depicts the construction of plasmid pGG A274.

Plasmid pSAR, FIG. 5, carries a translational fusion via a common Sau3A restriction site at the seventh/eighth signal sequence codon of the subtilisin genes of *B. subtilis* and *B. amyloliquefaciens*. As shown in FIG. 5, this gene, on an EcoRI-BamHI 2.0 Kb fragment, was subcloned into M13mp19 in order to isolate single-stranded template DNA to be used for site-directed mutagenesis to form pSAR-Q275R. The mutagenesis protocol was essentially that of Zoller, M., et al. (1983), *Methods Enzymol.*, 100, 468–500, (1) and used a synthetic oligonucleotide of the sequence:

above for site-directed mutagenesis using an oligonucleotide of the sequence:

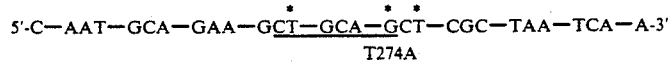
T274A in order to 1) introduce a PstI site at the same location in this gene corresponding to the site introduced into pSAR above and 2) to substitute the threonine at position 274 with alanine to form pGG36-T274A.

The mutant pSAR-Q275R and pGG36-T274A genes were individually subcloned back into pBS42 prior to PstI/BamHI digestions, fragment isolation and ligation to produce plasmid GG-A274B.amy.term. as shown in FIG. 5, all by standard methods.

A synthetic DNA linker was made by annealing complimentary single-stranded oligonucleotides of the sequences:

5'-G—ATC—GTC—GCG—TCG—ACC—GCA—CTA—CTC—ATT—TCT—GTT—GCT—TTT—AGT—TCA—T-3' and

Figure 6:
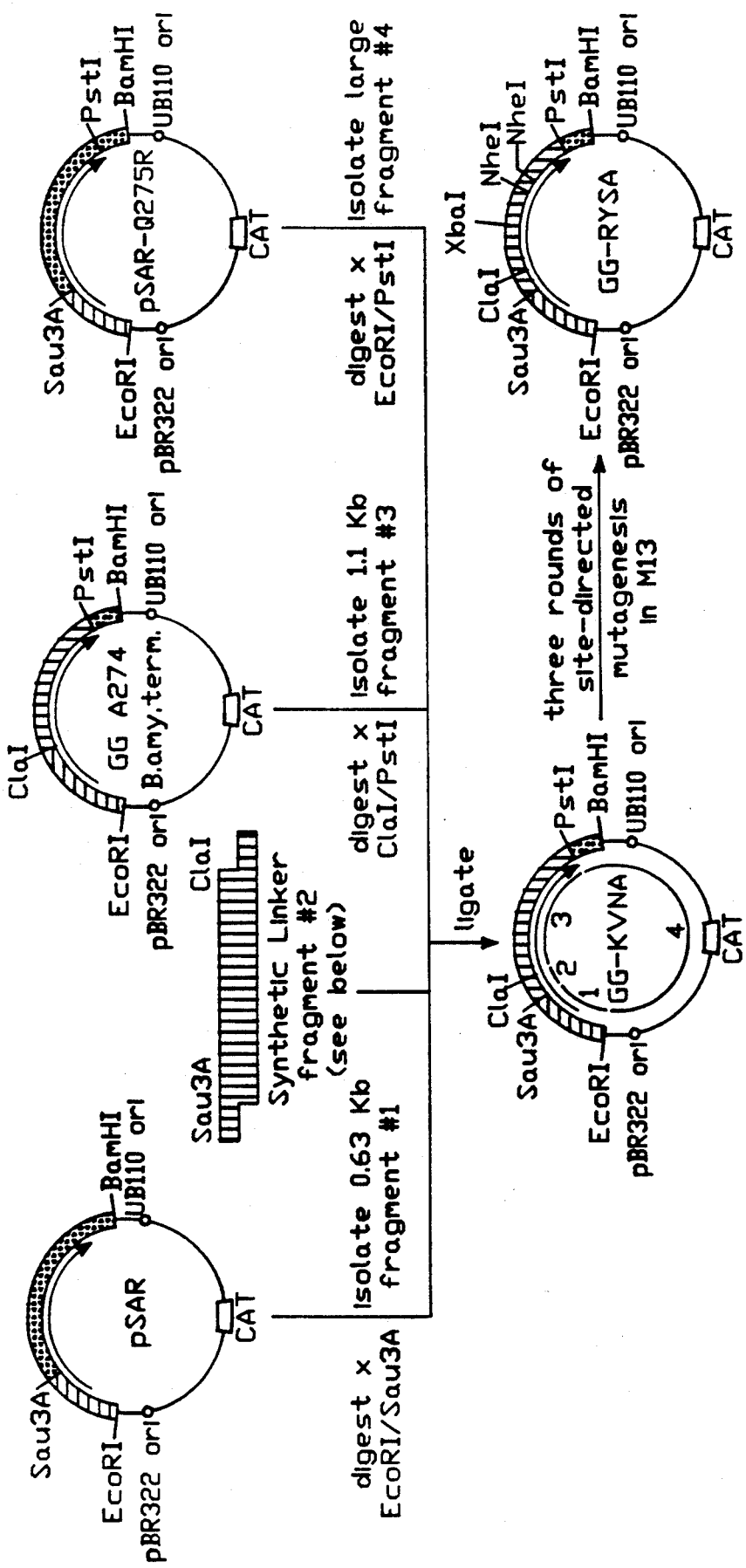
FIG. 6 depicts the construction of pGG-KVNA which is an intermediate to plasmid pGG-RYSA.

5'-CGA—TGA—ACT—AAA—AGC—AAC—AGA—AAT—GAG—TAG—TGC—GGT—CGA—CGC—GAC-3' to give the double-stranded DNA fragment #2 shown in FIG. 6. The recessed left- and right-hand ends of this duplex linker are complimentary to the Sau3A end of fragment #1 (from pSAR) and the ClaI end of fragment #3 (from pGG-A274 B.amy.term), respectively. These 3 fragments were combined with fragment 4 from pSAR-Q275R after restriction endonuclease digestions of plasmids, fragment isolation and ligation by standard methods to produce plasmid pGG-KVNA. The designation GG-KVNA indicates that this subtilisin contains

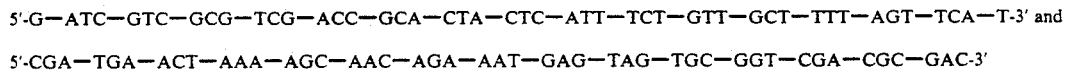
Q275R where the asterisks denote changes from the wild-type gene sequences and the underline represents an introduced PstI restriction endonuclease site used in screening for the particular mutant gene encoding the Q275R change. These changes were made to (1) convert the amino acid at this position to that found in *Bacillus lentus* subtilisin and (2) to allow hookup of the terminator in pSAR to the mature coding region of *Bacillus lentus* via a Pst site similarly introduced into pGG36 from *Bacillus lentus* (ATCC 21536).

Plasmid pGG36, FIG. 5, contains a 2.1 kb genomic

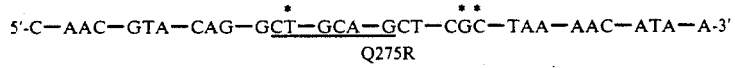

DNA fragment from *Bacillus lentus* (ATCC 21536) encoding the complete subtilisin gene which was cloned by standard methods in the shuttle vector pBS42. Band, L., et al. (1984), *DNA,*, 3, 17–21.

The amino acid sequence for this subtilisin is the same as that disclosed for subtilisin 309 in PCT Publication No. 89/06279. This gene was subcloned into M13 as the subtilisin encoded by pGG-36 which includes lysine (K) at position 27, valine (V) at position 104, asparagine (N) at position 123 and the substitution of threonine at position 274 with alanine (A).

EXAMPLE 2

Modification of PGG-KVNA

As indicated in FIG. 6, the GG-KVNA gene (2.1 kb EcoRI-BamHI fragment) was subcloned into M13 for three successive rounds of site-directed mutagenesis using oligonucleotides having the sequence:

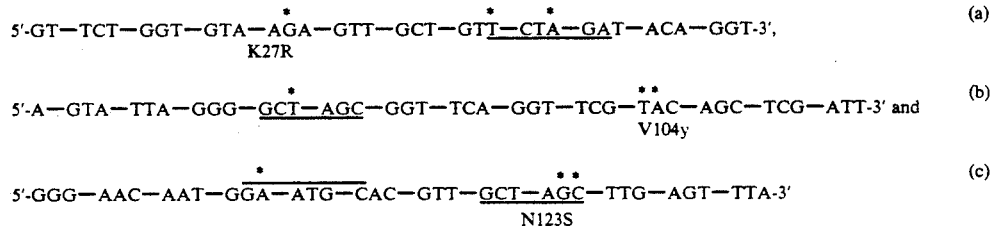

The asterisks denote changes from the wild-type gene sequence. The underlines represent, in (a) an introduced XbaI site and in (b) and (c) introduced NheI sites used to screen for the presence of the linked R27, Y104 and S123 mutations, respectively. In addition, in (c), the overlined denotes a destroyed SphI site. Finally, the 2.1 kb GG-RYSA gene was subcloned back into pBS42 for expression in *B. subtilis* hosts.

The resultant plasmid was designated pGG-RYSA. This designation indicates that four residues were modified in the pGG-KVNA plasmid. Lysine (K) at position 27 to arginine (R), valine (V) to tyrosine (Y) at position 104 and asparagine (N) at position 123 to serine (S). The alanine previously substituted at residue 274 was not modified in this procedure.

The lysine at position 27 was substituted with arginine based upon the amino acid sequencing of subtilisin 309. As indicated in PCT Publication No. WO89/06279, lysine is located at position 27. However, after independently sequencing this subtilisin protein, the initial data indicated that arginine was the residue at position 27. In the case of the substitution of tyrosine for valine at residue 104, the substitution was made to lower the pH activity profile and to increase the performance of the enzyme based on results previously obtained for *Bacillus amyloliquefaciens* subtilisin (sometimes referred to as BPN'). The substitution of asparagine at position 123 with serine is based on the results obtained hereinafter wherein it was determined that the substitution of serine at position 123 maximized the proteolytic activity of the enzyme in a closely related mutant.

EXAMPLE 3

Construction of Synthetic *Bacillus lentus* Subtilisin Gene

DNA encoding the amino acid sequence of *Bacillus lentum* subtilisin was also prepared by constructing a gene encoding a synthetic DNA sequence.

Figure 7:
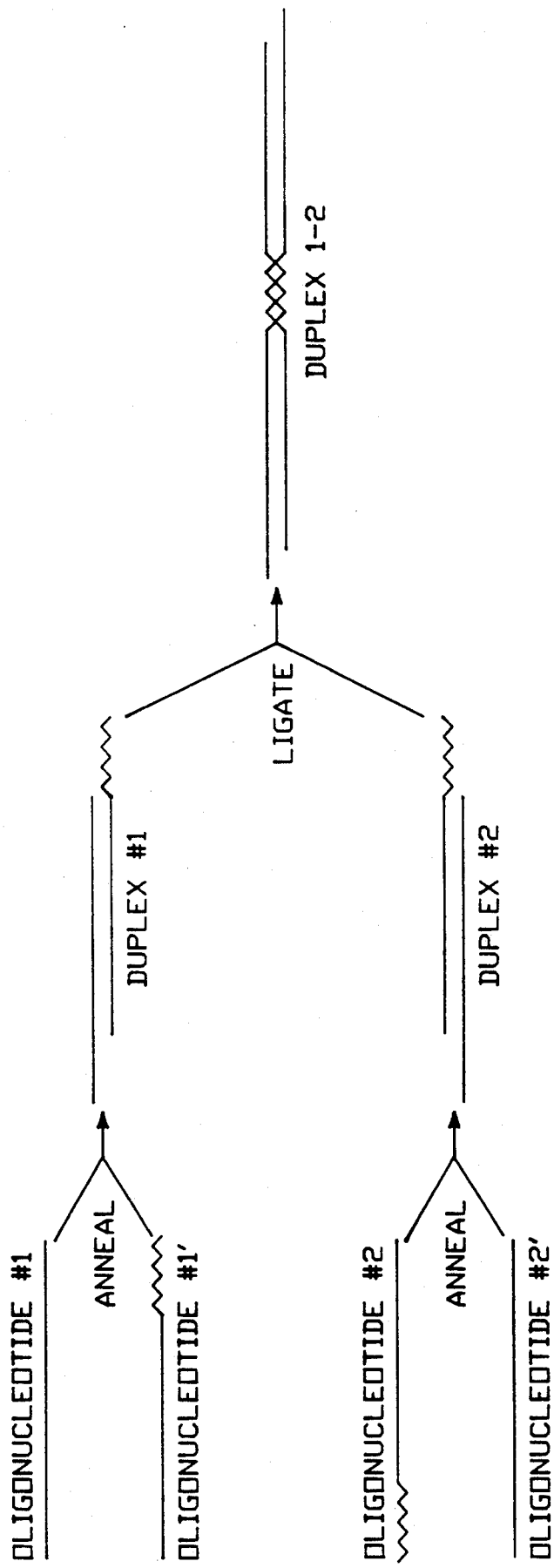
FIG. 7 depicts the oligonucleotide-duplex method used to construct a synthetic *Bacillus lentus* subtilisin gene.

The 2.1 kb HindIII genomic fragment from plasmid pGG36 was sequenced. The deduced amino acid sequence of the mature gene product (GG36 subtilisin) was used to design a synthetic mature coding sequence with the following properties: (1) In general, the codons most frequently found for each amino acid in seven different *B. subtilis* genes (from a tabulation of codon usages, Table 2 from Maruyama, T., et al., (1986), *Nucl. Acids Res.*, Supplement 14 pp. r151-r197) were utilized except in the cases where alternate codons resulted in conveniently located restriction enzyme recognition sites within the gene; (2) Approximately every 40-60 b.p. of the ~0.8 mature coding region, combinations of 2 or 3 specifically chosen codons were utilized which resulted in the introduction of fairly evenly spaced, unique restriction sites. These sites were chosen to facilitate (a) later cassette mutagenesis and screening studies and (b) constructions involving more than one mutation; (3) A unique Pst I recognition site was designed to cover codons 272-274 allowing hook up to the terminator sequences of a *Bacillus amyloliquefaciens* gene similarly modified over the same three codons and substituting threonine at position 274 with alanine; and (4) A unique NruI site was introduced to cover mature codons residues 9-10 allowing hookup to GG36's pre-pro coding sequence via a short synthetic duplex DNA linker. Based on this design, oligonucleotides ("oligos") were synthesized such that upon annealing the coding and non-coding oligos for a given ~60 b.p. coding region, the resultant duplex DNA fragment would have at it's ends single stranded regions complimentary to the end of the next duplex fragment of the gene (see, FIG. 7).

Figure 8:
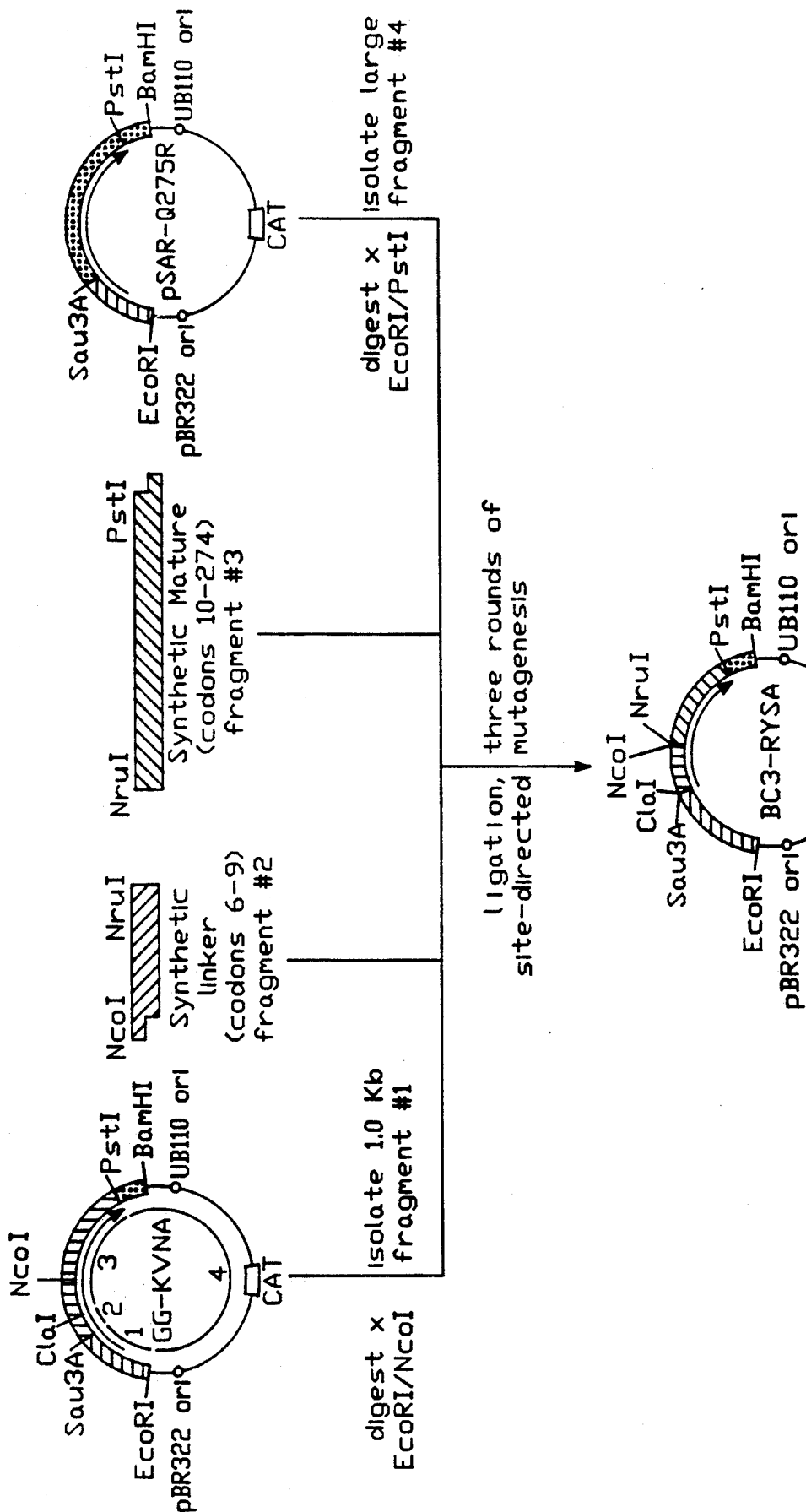
FIG. 8 depicts the strategy for constructing a synthetic gene encoding *Bacillus lentus* subtilisin.

A total of 36 separate oligos (comprising 18 individual duplexes) were used in the scheme, as outlined above, resulting in an ~0.8 kb duplex synthetic mature coding region (Fragment 3 in FIG. 8).

Finally, one additional pair or synthetic oligo's was synthesized, which upon annealing (to give fragment 2 in FIG. 8) has an NcoI site at it's 5' end (complimentary to GG36's NcoI site at mature codons 5-6) and an NruI site at its 3' end (complimentary to the 3's 5' end of fragment 3).

The final construction to give a complete expression unit consisting of *B. subtilis* promoter and the first seven amino acids of the signal sequence hooked up to GG36's sequences encoding the remainder of the signal sequence, the complete pro sequence and the first six mature amino acids (Fragment 1 from GG-KVNA), the synthetic gene encoding mature residues 7-274 (Fragments 2+3) and the terminator region (including the final mature gene codon 279) of *Bacillus amyloliquefaciens* (fragment 4) was done as a four-way ligation as set forth in FIG. 6.

Finally, three additional separate mutations were introduced into the mature coding region of this full length hybrid gene. The first substituted the lysine at position 27 with arginine. The second substituted the valine at position 104 with tyrosine. The third substituted the asparagine at position 123 with serine The resultant plasmid is designated pBC3-RYSA. The following example describes the method used to modify position 123 in the synthetic gene. Similar methods were used to modify positions 27 and 104 in this synthetic gene.

EXAMPLE 4

Construction of Position 123 Mutants

An Xho I site was introduced over codons 111/112 in the synthetic gene from Example 3 by making three phenotypically silent mutations via site directed mutagenesis (primer extension mutagenesis in M13). The resulting plasmid, pX123 (FIG. 9), was digested with Xho I and Ava I and the large vector-containing fragment isolated by electroelution from agarose gel. Complimentary synthetic oligonucleotides were annealed, ligated with the pX123 large fragment and transformed into *E. coli* strain MM294. These cassettes encoded, individually, all 20 naturally-occurring amino acids at position 123, and in addition contained a silent mutation which destroyed a unique Sph I site lying between the Xho I and Ava I sites in pX123. Resulting plasmids from *E. coli* transformants were screened for the loss of the unique Sph I site. Positives by restriction analysis (i.e., Sph I negatives) were sequenced to confirm the presence of the desired position 123 mutations subcloned into the shuttle vector pBS42 and transformed into *Bacillus subtilis* BG2036 for expression.

EXAMPLE 5

Activity of Various +123 Mutants

Proteolytic activity of each of the subtilisin mutants encoded by the above modified position +123 mutants was assayed by mixing 0.04 ml of supernatant from centrifuged culture broths with 0.56 ml of 1% w/v casein in 0.1 M Tris pH 8.60. After a 20 minute incubation at 37° C., reactions were quenched by precipitation with 10% trichloroacetic acid (TCA). Activity was determined from the absorbance at a wavelength of 280 nm for the supernatant after precipitation with 10% TCA.

TABLE I

Relative proteolytic activity of codon 123 variants normalized to Asn-123 mutant

| Codon 123 | % Proteolytic Activity |
| --- | --- |
| Ser | 116 |
| Asn | 100 |
| Cys | 22 |
| Gly | 12 |
| Ala | 9 |
| Thr | 7 |
| Gln | 7 |
| Val | 6 |
| Glu | <5 |
| Ile | <5 |
| Trp | <5 |
| Phe | <5 |
| Asp | <5 |
| His | <5 |
| Leu | <5 |
| Met | <5 |
| Pro | <5 |
| Tyr | <5 |

In the process of final confirmation of the DNA sequence of the synthetic gene coding for the enzyme BC3-RYSA, proline was found to be at position 78 instead of serine (the amino acid at this position in *Bacillus lenus* subtilisin). The initial properties of the position 123 mutations were tested in this enzyme, BC3-RPYA (proline at position 78). These results are shown in Table I. The amino acid at position 78 was thereafter changed back to serine to form the DNA and amino acid sequence shown in FIG. 10 by replacing the synthetic DNA duplex corresponding to that portion of the gene.

As can be seen the substitution of Asn with Ser at position +123 results in a substantial increase in proteolytic activity. The relationship between the various subtilisins discussed herein are summarized for positions 27, 78, 104, 123 and 274 in Table II.

TABLE II

| | position | | | | |
| --- | --- | --- | --- | --- | --- |
| | 27 | 78 | 104 | 123 | 274 |
| GC36 (genomic) | Lys(K) | Ser(S) | Val(V) | Asn(N) | Thr(T) |
| Synthetic B. lentus gene | Lys(K) | Pro(P) | Val(V) | Asn(N) | Ala(A) |
| B.amyloliquefacins subtilisin (BPN) | Lys(K) | Ser(S) | Tyr(Y) | Asn(N) | Ala(A) |
| Subtilisin 309 as published | Lys(K) | Ser(S) | Val(V) | Asn(N) | Thr(T) |
| Preferred embodiment herein | Arg(R) | Ser(S) | Tyr(Y) | Ser(S) | Ala(A) |

EXAMPLE 6

Stability of Position 274 Mutants

Stability of position 274 mutants in BC3-RPY (arginine at position 27, proline at position 78, and tyrosine at position 104 in *Bacillus lentus* subtilisin) are shown in Table III. Data are percent activity remaining following incubation at 37° C. in 50 mM EDTA for 60 minutes.

TABLE III

| Amino Acid at Position 274 | % Activity |
| --- | --- |
| Leucine | 2% |
| Serine | 79% |
| Threonine | 91% |
| Valine | 42% |
| Alanine | 43% |

Mutations at this position clearly effect stability of the enzyme. Although the alanine mutation was not as stable as serine or threonine at this position, this enzyme provided superior performance relative to *Bacillus lentus* subtilisin under the conditions of use described. For different applications, other amino acids at position 274 may be used.

EXAMPLE 7

Detergent Composition

A spray-dried phosphate detergent granule of the following composition was prepared:

| Component | Weight % |
| --- | --- |
| Sodium C12 linear alkylbenzene sulfonate | 8.45 |
| Sodium Tallow Alcohol sulfate | 4.23 |
| Sodium C14~15 linear alkyl sulfate | 4.23 |
| Sodium Toluene Sulfonate | 1.00 |
| Sodium Tripolyphosphate | 5.60 |
| Sodium pyrophosphate | 22.40 |
| Silicate (1.6 r) | 5.50 |
| Sodium Sulfate | 29.83 |
| Sodium polyacrylate (4500 MW) | 1.17 |
| Brightener | 0.22 |
| Sodium Carbonate | 12.30 |
| Polyethylene Glycol (MW 8000) | 0.47 |
| C12~13 alcohol polyethoxylate (6.5)* | 0.50 |
| Miscellaneous + Water | to 100% |
| Protease** | 0.034 |

*Alcohol and monoethoxylate alcohol removed.
**mg active enzyme/g (2.0 mg active enzyme/g stock)

A 0.1 weight percent solution of this composition in water had a pH of 10.0. The composition with subtilisin mutant of the invention (FIG. 7) provided superior cleaning of enzyme-sensitive stains, when compared to *Bacillus lentus* at 0.068 mg active enzyme/g product, in a 95° F. (35° C.) wash at 6 grains per gallon (gpg) hardness (3:1 Ca/Mg).

Throughout this application reference is made to various amino acids by way of common one-and three-letter codes. Such codes are identified in *Proteins: Structures and Molecular Proteases*, Thomas E. Creighton, eds. W. N. Freeman, N.Y., N.Y. (1983), p. 3.

Although the preferred form of the invention has been described above, it will be obvious to those skilled in the art to which the invention pertains, that, after understanding the invention as a whole, various changes and equivalent modifications may be made without departing from the scope of the invention as defined by the appended claims.

All publications are expressly incorporated herein by reference.

What is claimed is:

1. An enzymatic cleaning composition capable of degrading proteins comprising:
   a) a surfactant end; and
   b) a subtilisin mutant having an amino acid sequence not found in nature which is derived from a precursor subtilisin by substituting a different amino acid for the amino acid residue at a position in said precursor equivalent to +123 or +274 in *Bacillus amyloliquefaciens* subtilisin.

2. The composition of claim 1 wherein said subtilisin has the following amino acid sequence:

AQSVPWGISRVQAPAAHNRGLTGSGVRVAVLDTGISTHPDLNIRGGASFVPGE
PSTQDGNGHGTHVAGTIAALNNSIGVLGVAPSAELYAVKVLGASGSGSYSSIA
QGLEWAGNNGMHVASLSLGSPSPSATLEQAVNSATSRGVLVVAASGNSGAGSI
SYPARYANAMAVGATDQNNNRASFSQYGAGLDIVAPGVNVQSTYPGSTYASLN
GTSMATPHVAGAAALVKQKNPSWSNVQIRNHLKNTATSLGSTNLYGSGLVNAE
AAAR.

3. The composition of claim 1 wherein the surfactant comprises a detergent.

4. A composition according to claim 1 comprising a spray-dried detergent granule.

* * * * *